US012324671B2

(12) United States Patent
Relan et al.

(10) Patent No.: US 12,324,671 B2
(45) Date of Patent: Jun. 10, 2025

(54) SYSTEM, METHOD, AND APPARATUS FOR MAPPING LOCAL ACTIVATION TIMES

(71) Applicant: St. Jude Medical, Cardiology Divsion, Inc., St. Paul, MN (US)

(72) Inventors: Jatin Relan, Bordeaux (FR); Valtino X. Afonso, Oakdale, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 230 days.

(21) Appl. No.: 17/911,605

(22) PCT Filed: Dec. 22, 2020

(86) PCT No.: PCT/US2020/066535
§ 371 (c)(1),
(2) Date: Sep. 14, 2022

(87) PCT Pub. No.: WO2021/188182
PCT Pub. Date: Sep. 23, 2021

(65) Prior Publication Data
US 2023/0119399 A1      Apr. 20, 2023

Related U.S. Application Data

(60) Provisional application No. 62/990,267, filed on Mar. 16, 2020.

(51) Int. Cl.
*A61B 5/339* (2021.01)
*A61B 5/00* (2006.01)
(Continued)

(52) U.S. Cl.
CPC .............. *A61B 5/339* (2021.01); *A61B 5/347* (2021.01); *A61B 5/367* (2021.01); *A61B 5/7203* (2013.01); *A61B 5/7221* (2013.01); *A61B 5/7475* (2013.01)

(58) Field of Classification Search
CPC .......... A61B 5/287; A61B 5/339; A61B 5/347; A61B 5/367; A61B 5/6858; A61B 5/7203;
(Continued)

(56) References Cited

U.S. PATENT DOCUMENTS

| | | |
|---|---|---|
| 5,697,377 A | 12/1997 | Wlittkampf |
| 5,983,126 A | 11/1999 | Wlittkampf |

(Continued)

FOREIGN PATENT DOCUMENTS

| | | |
|---|---|---|
| JP | 2018-202130 A | 12/2018 |
| JP | 2019-103614 A | 6/2019 |

OTHER PUBLICATIONS

International Search Report and Written Opinion for PCT/US2020/066535 mailed Apr. 12, 2021.

*Primary Examiner* — George Manuel
(74) *Attorney, Agent, or Firm* — Wiley Rein LLP

(57) ABSTRACT

An electroanatomical mapping system graphically represents local activation time (LAT) information contained in data set including a plurality of electrophysiology (EP) data points. The system computes a spatial gradient over a spatial kernel centered at an EP data point and a plurality of temporal gradients for the EP data points set. Using the gradients, the electroanatomical mapping system can detect spatial outlier EP data points and temporal outlier EP data points. These outlier EP data points can then be corrected prior to outputting a graphical representation of the LAT map on a model of a cardiac surface.

19 Claims, 9 Drawing Sheets

(51) Int. Cl.
*A61B 5/347* (2021.01)
*A61B 5/367* (2021.01)

(58) Field of Classification Search
CPC ..... A61B 5/7207; A61B 5/7221; A61B 5/726;
A61B 5/7278; A61B 5/7425; A61B
5/743; A61B 5/7475
See application file for complete search history.

(56) References Cited

U.S. PATENT DOCUMENTS

| | | |
|---|---|---|
| 6,301,496 B1 | 10/2001 | Reisfeld |
| 6,640,119 B1 | 10/2003 | Budd et al. |
| 6,728,562 B1 | 4/2004 | Budd et al. |
| 6,939,309 B1 | 9/2005 | Beatty et al. |
| 6,947,785 B1 | 9/2005 | Beatty et al. |
| 6,978,168 B2 | 12/2005 | Beatty et al. |
| 6,990,370 B1 | 1/2006 | Beatty et al. |
| 7,263,397 B2 | 8/2007 | Hauck |
| 7,885,707 B2 | 2/2011 | Hauck |
| 10,398,331 B2 | 9/2019 | Relan et al. |
| 10,542,888 B2 | 1/2020 | Zeidan et al. |
| 10,888,235 B2 | 1/2021 | Hagfors et al. |
| 11,071,486 B2 | 7/2021 | Honicker |
| 11,096,617 B2 | 8/2021 | Han et al. |
| 2017/0251942 A1* | 9/2017 | Brodnick ............. A61B 5/7221 |
| 2017/0281031 A1 | 10/2017 | Houben et al. |
| 2019/0030332 A1 | 1/2019 | Ghosh et al. |
| 2019/0038165 A1 | 2/2019 | Relan et al. |

\* cited by examiner

SYSTEM, METHOD, AND APPARATUS FOR MAPPING LOCAL ACTIVATION TIMES

CROSS-REFERENCE TO RELATED APPLICATIONS

This application claims the benefit of U.S. provisional application No. 62/990,267, filed 16 Mar. 2020, which is hereby incorporated by reference in its entirety as though fully set forth herein.

BACKGROUND

The present disclosure relates generally to electrophysiological visualization and mapping. More specifically, the present disclosure relates to a system, method, and apparatus for generating visualizations of local activation times.

Electrophysiological mapping, and more particularly electrocardiographic mapping, is a part of numerous cardiac diagnostic and therapeutic procedures. As the complexity of such procedures increases, however, the electrophysiology maps utilized must increase in quality, in density, and in the rapidity and ease with which they can be generated.

Electrophysiology studies can include the creation of a local activation time (LAT) map. LAT maps can, for example, provide insight to a practitioner as to how an arrhythmia is traveling throughout the cardiac chambers. Indeed, those of ordinary skill in the art will be familiar with the graphical presentation of LAT maps in electroanatomical mapping systems.

Extant electroanatomical mapping systems, however, can occasionally exhibit anomalous LAT spikes in their graphical representations of LAT maps. These spikes are referred to herein as "outliers."

There are several causes of outliers. For instance, for highly complex convex anatomical geometries, such as the left atrial appendage or ventricular apex, the stacking of electrophysiology data points within the middle of the convexity can lead to incorrect projections onto the surface.

As another example, where electrophysiology data points are very close to each other and thus clustered into a duplicate set, an incorrect LAT selection for the duplicate set can result in an outlier.

As yet another example, complex electrograms with low amplitude, long, and fractionated potentials, as may be encountered in low-voltage myocardium, can make it challenging to correctly determine the LAT and lead to an outlier.

Outliers can also result from cardiac and/or respiratory motion or from mechanical artifacts, such as catheter splines contacting each other during the collection of some, but not all, electrophysiology data points.

BRIEF SUMMARY

Disclosed herein is a method of graphically representing local activation time (LAT), including the following steps: receiving, at an electroanatomical mapping system, an LAT data set including a plurality of electrophysiology (EP) data points, wherein each EP data point of the plurality of EP data points includes localization information and an electrogram signal; the electroanatomical mapping system computing a spatial gradient over a spatial kernel centered at an EP data point of the plurality of EP data points of the LAT data set; the electroanatomical mapping system computing a respective temporal gradient for each of the plurality of EP data points of the LAT data set, thereby computing a plurality of temporal gradients; the electroanatomical mapping system detecting a spatial outlier EP data point within the spatial kernel using the spatial gradient; the electroanatomical mapping system detecting a temporal outlier EP data point using the plurality of temporal gradients; the electroanatomical mapping system correcting the spatial outlier EP data point and the temporal outlier EP data point, thereby creating a corrected LAT map; and the electroanatomical mapping system outputting a graphical representation of the corrected LAT map on a model of a cardiac surface.

In embodiments of the disclosure, receiving, at an electroanatomical mapping system, an LAT data set including a plurality of electrophysiology (EP) data points, can include: projecting each EP data point onto the model of the cardiac surface using the localization information for the respective EP data point; and assigning a LAT to each projected EP data point using the electrogram signal for the respective EP data point.

According to aspects of the instant disclosure, the electroanatomical mapping system can define a spatial kernel for each EP data point of the plurality of EP data points and compute a spatial gradient for each defined spatial kernel. Alternatively, the electroanatomical mapping system can accept user input selecting a subset of the plurality of EP data points, define a spatial kernel for each EP data point of the subset of the plurality of EP data points, and compute a spatial gradient for each defined spatial kernel. In still further embodiments, the electroanatomical mapping system can identify a high LAT gradient region within the LAT data set, define a spatial kernel for each EP data point within the high LAT gradient region, and compute a spatial gradient for each defined spatial kernel.

It is contemplated that the electroanatomical mapping system will detect the spatial outlier EP data point by comparing the spatial gradient to a spatial gradient threshold. The spatial gradient threshold can be a user-preset value or a computed scaled mean absolute deviation value.

Similarly, the electroanatomical mapping system can detect the temporal outlier EP data point by comparing the plurality of temporal gradients to a temporal gradient threshold. The temporal gradient threshold can be a user-preset value or a computed scaled mean absolute deviation value.

In embodiments of the disclosure, the electroanatomical mapping system correcting the spatial outlier EP data point and the temporal outlier EP data point, thereby creating a corrected LAT map, includes the electroanatomical mapping system applying at least one of a LAT value dispersion algorithm and a peak frequency dispersion algorithm to the spatial outlier EP data point and the temporal outlier EP data point.

Optionally, the method can include the electroanatomical mapping system spatially smoothing the LAT data set. For instance, the electroanatomical mapping system can apply a Gaussian distribution to the spatial kernel.

Also disclosed herein is a method of graphically representing local activation time (LAT), including the following steps: receiving, at an electroanatomical mapping system, an LAT map, the LAT map including a plurality of electrophysiology (EP) data points; the electroanatomical mapping system identifying at least one of a spatial outlier EP data point and a temporal outlier data point within the plurality of EP data points; the electroanatomical mapping system correcting the identified at least one of the spatial outlier EP data point and the temporal outlier EP data point, thereby creating a corrected LAT map; and the electroanatomical mapping system outputting a graphical representation of the corrected LAT map on a model of a cardiac surface.

In aspects of the disclosure, the electroanatomical mapping system identifies the at least one of a spatial outlier EP data point and a temporal outlier EP data point within the plurality of EP data points by: computing a spatial gradient over a spatial kernel centered at an EP data point of the plurality of EP data points; computing a temporal gradient over a temporal kernel for the EP data point of the plurality of EP data points; and identifying the at least one of the spatial outlier EP data point and the temporal outlier EP data point using the computed spatial gradient and the computed temporal gradient.

The electroanatomical mapping system can correct the identified at least one of the spatial outlier EP data point and the temporal outlier EP data point, thereby creating a corrected LAT map, comprises the electroanatomical mapping system by applying at least one of a LAT value dispersion algorithm and a peak frequency dispersion algorithm to the at least one of the spatial outlier EP data point and the temporal outlier EP data point.

The instant disclosure also provides a system for graphically representing local activation time (LAT). The system includes a visualization module configured to: receive an LAT data set including a plurality of electrophysiology (EP) data points, wherein each EP data point of the plurality of EP data points includes localization information and an electrogram signal; compute a spatial gradient over a spatial kernel centered at an EP data point of the plurality of EP data points of the LAT data set; compute a respective temporal gradient for each of the plurality of EP data points of the LAT data set, thereby computing a plurality of temporal gradients; detect a spatial outlier EP data point within the spatial kernel using the spatial gradient; detect a temporal outlier EP data point using the plurality of temporal gradients; correct the spatial outlier EP data point and the temporal outlier EP data point, thereby creating a corrected LAT map; and output a graphical representation of the corrected LAT map on a model of a cardiac surface.

The visualization module can be configured to identify a high LAT gradient region within the LAT data set and compute a plurality of spatial gradients over a respective plurality of spatial kernels, each of the plurality of spatial kernels centered at a respective EP data point within the high LAT gradient region.

The visualization module can also be configured to correct the spatial outlier EP data point and the temporal outlier EP data point by applying at least one of a LAT value dispersion algorithm and a peak frequency dispersion algorithm to the spatial outlier EP data point and the temporal outlier EP data point.

The foregoing and other aspects, features, details, utilities, and advantages of the present invention will be apparent from reading the following description and claims, and from reviewing the accompanying drawings.

While multiple embodiments are disclosed, still other embodiments of the present disclosure will become apparent to those skilled in the art from the following detailed description, which shows and describes illustrative embodiments. Accordingly, the drawings and detailed description are to be regarded as illustrative in nature and not restrictive.

DETAILED DESCRIPTION

The present disclosure provides systems, methods, and apparatus for the visualization of electrophysiology maps (e.g., electrocardiographic maps). For purposes of illustration, several exemplary embodiments will be described in detail herein with reference to cardiac electrophysiology procedures. More specifically, aspects of the disclosure will be described in the context of the visualization of local activation time (LAT) maps using electrophysiology (EP) data points collected using a high density (HD) grid catheter, such as the Advisor™ HD grid mapping catheter from Abbott Laboratories (Abbott Park, Illinois), in conjunction with an electroanatomical mapping system, such as the EnSite Precision™ cardiac mapping system, also from Abbott Laboratories. Those of ordinary skill in the art will understand, however, how to apply the teachings herein to good advantage in other contexts and/or with respect to other devices.

Figure 1:
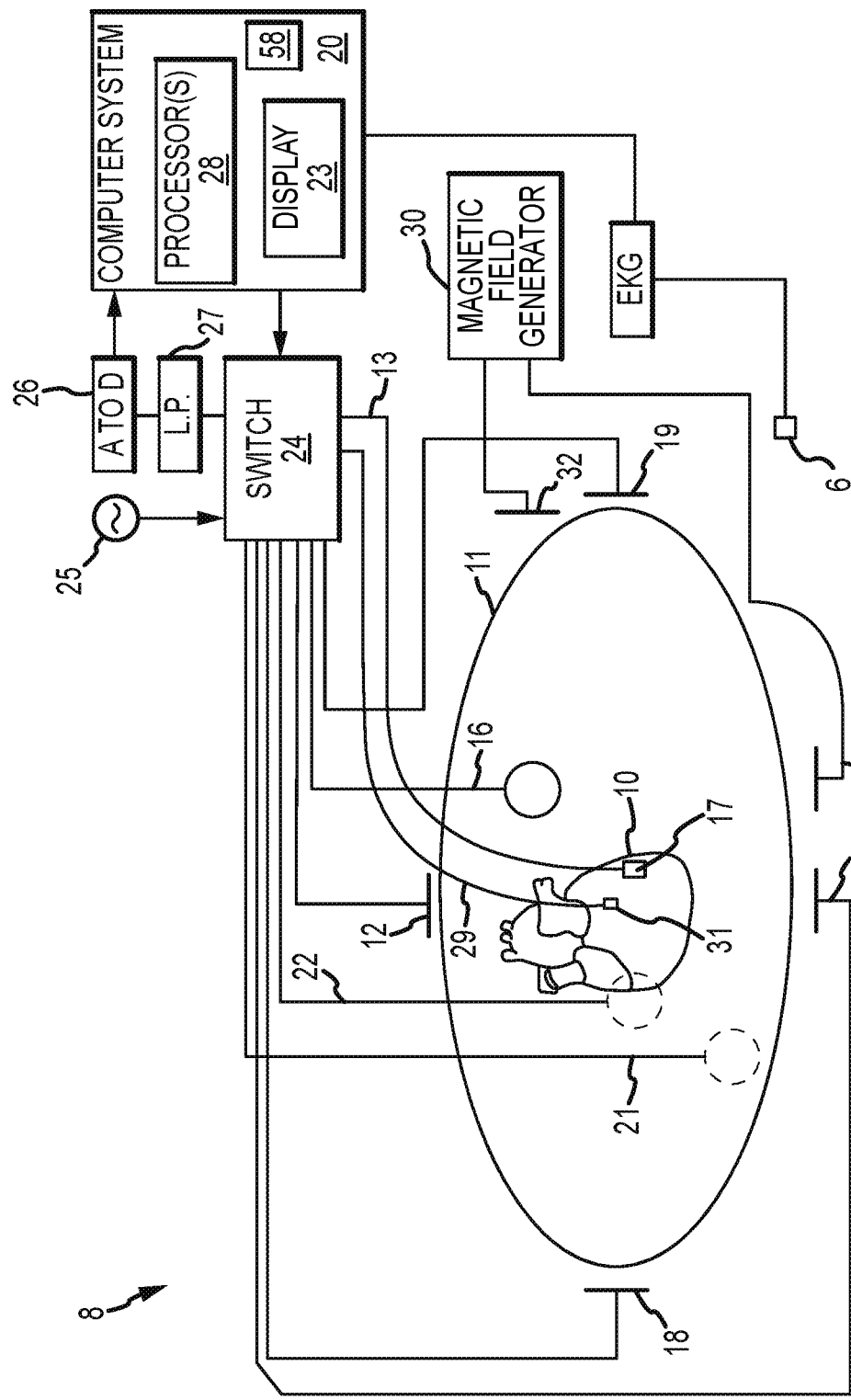
FIG. 1 is a schematic diagram of an exemplary electroanatomical mapping system.

FIG. 1 shows a schematic diagram of an exemplary electroanatomical mapping system 8 for conducting cardiac electrophysiology studies by navigating a cardiac catheter and measuring electrical activity occurring in a heart 10 of a patient 11 and three-dimensionally mapping the electrical activity and/or information related to or representative of the electrical activity so measured. System 8 can be used, for example, to create an anatomical model of the patient's heart 10 using one or more electrodes. System 8 can also be used to measure electrophysiology data at a plurality of points along a cardiac surface and store the measured data in association with location information for each measurement point at which the electrophysiology data was measured, for example to create a diagnostic data map of the patient's heart 10.

As one of ordinary skill in the art will recognize, system 8 determines the location, and in some aspects the orientation, of objects, typically within a three-dimensional space, and expresses those locations as position information determined relative to at least one reference. This is referred to herein as "localization."

For simplicity of illustration, the patient 11 is depicted schematically as an oval. In the embodiment shown in FIG. 1, three sets of surface electrodes (e.g., patch electrodes) are shown applied to a surface of the patient 11, defining three generally orthogonal axes, referred to herein as an x-axis, a y-axis, and a z-axis. In other embodiments the electrodes could be positioned in other arrangements, for example multiple electrodes on a particular body surface. As a further alternative, the electrodes do not need to be on the body surface, but could be positioned internally to the body.

In FIG. 1, the x-axis surface electrodes 12, 14 are applied to the patient along a first axis, such as on the lateral sides of the thorax region of the patient (e.g., applied to the patient's skin underneath each arm) and may be referred to as the Left and Right electrodes. The y-axis electrodes 18, 19 are applied to the patient along a second axis generally orthogonal to the x-axis, such as along the inner thigh and neck regions of the patient, and may be referred to as the Left Leg and Neck electrodes. The z-axis electrodes 16, 22 are applied along a third axis generally orthogonal to both the x-axis and the y-axis, such as along the sternum and spine of the patient in the thorax region, and may be referred to as the Chest and Back electrodes. The heart 10 lies between these pairs of surface electrodes 12/14, 18/19, and 16/22.

An additional surface reference electrode (e.g., a "belly patch") 21 provides a reference and/or ground electrode for the system 8. The belly patch electrode 21 may be an alternative to a fixed intra-cardiac electrode 31, described in further detail below. It should also be appreciated that, in addition, the patient 11 may have most or all of the conventional electrocardiogram ("ECG" or "EKG") system leads in place. In certain embodiments, for example, a standard set of 12 ECG leads may be utilized for sensing electrocardiograms on the patient's heart 10. This ECG information is available to the system 8 (e.g., it can be provided as input to computer system 20). Insofar as ECG leads are well understood, and for the sake of clarity in the figures, only a single lead 6 and its connection to computer 20 is illustrated in FIG. 1.

A representative catheter 13 having at least one electrode 17 is also shown. This representative catheter electrode 17 is referred to as the "roving electrode," "moving electrode," or "measurement electrode" throughout the specification. Typically, multiple electrodes 17 on catheter 13, or on multiple such catheters, will be used. In one embodiment, for example, the system 8 may comprise sixty-four electrodes on twelve catheters disposed within the heart and/or vasculature of the patient. In other embodiments, system 8 may utilize a single catheter that includes multiple (e.g., eight) splines, each of which in turn includes multiple (e.g., eight) electrodes.

Figure 2:
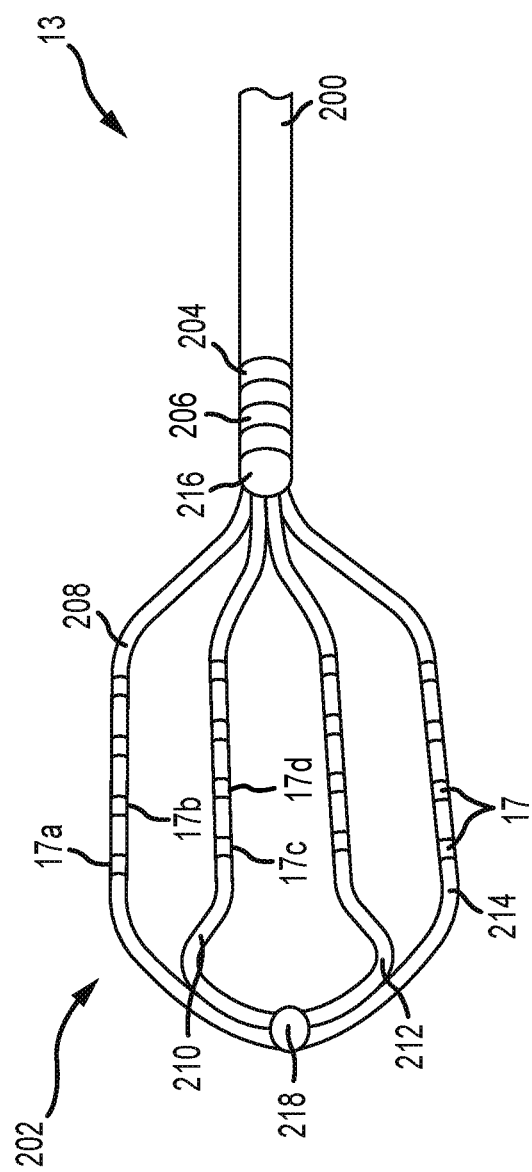
FIG. 2 depicts an exemplary catheter that can be used in connection with aspects of the instant disclosure.

The foregoing embodiments are merely exemplary, however, and any number of electrodes and/or catheters may be used. For example, for purposes of this disclosure, a segment of an exemplary multi-electrode catheter, and in particular an HD grid catheter, is shown in FIG. 2. HD grid catheter 13 includes a catheter body 200 coupled to a paddle 202. Catheter body 200 can further include first and second body electrodes 204, 206, respectively. Paddle 202 can include a first spline 208, a second spline 210, a third spline 212, and a fourth spline 214, which are coupled to catheter body 200 by a proximal coupler 216 and to each other by a distal coupler 218. In one embodiment, first spline 208 and fourth spline 214 can be one continuous segment and second spline 210 and third spline 212 can be another continuous segment. In other embodiments, the various splines 208, 210, 212, 214 can be separate segments coupled to each other (e.g., by proximal and distal couplers 216, 218, respectively). It should be understood that HD catheter 13 can include any number of splines; the four-spline arrangement shown in FIG. 2 is merely exemplary.

As described above, splines 208, 210, 212, 214 can include any number of electrodes 17; in FIG. 2, sixteen electrodes 17 are shown arranged in a four-by-four array. It should also be understood that electrodes 17 can be evenly and/or unevenly spaced, as measured both along and between splines 208, 210, 212, 214. For purposes of easy reference in this description, FIG. 3A provides alphanumeric labels for electrodes 17.

As those of ordinary skill in the art will recognize, any two neighboring electrodes 17 define a bipole. Thus, the 16 electrodes 17 on catheter 13 define a total of 42 bipoles-12 along splines (e.g., between electrodes 17a and 17b, or between electrodes 17c and 17d), 12 across splines (e.g., between electrodes 17a and 17c, or between electrodes 17b and 17d), and 18 diagonally between splines (e.g., between electrodes 17a and 17d, or between electrodes 17b and 17c).

Figure 3B:
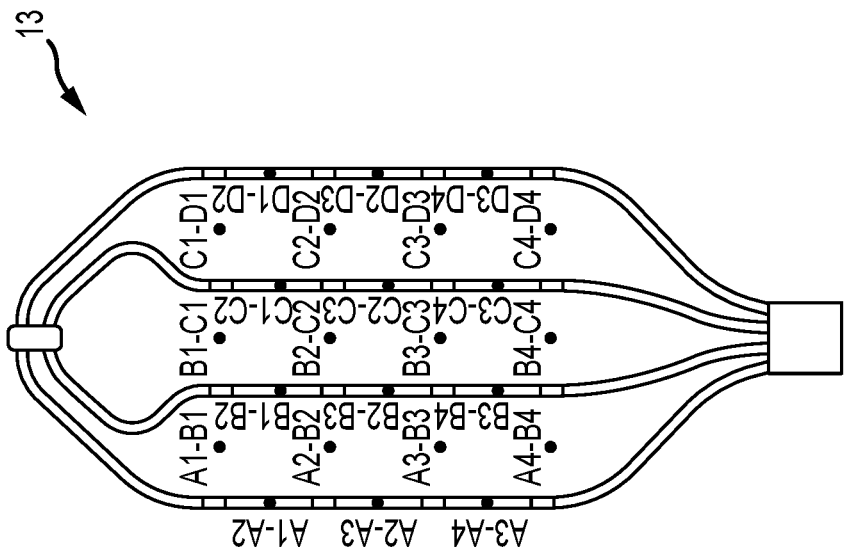
FIGS. 3A and 3B provide alphanumeric labeling conventions for electrodes carried by a multi-electrode catheter and the bipoles associated therewith.
Figure 3A:
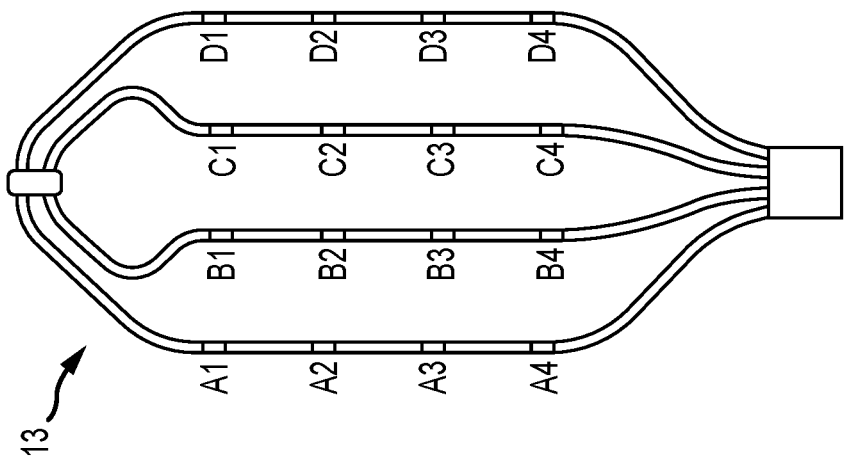

For ease of reference in this description, FIG. 3B provides alphanumeric labels for the along- and across-spline bipoles. FIG. 3B omits alphanumeric labels for the diagonal bipoles, but this is only for the sake of clarity in the illustration. It is expressly contemplated that the teachings herein can also be applied with respect to the diagonal bipoles.

Any bipole can, in turn, be used to generate a bipolar electrogram according to techniques that will be familiar to those of ordinary skill in the art. Moreover, these bipolar electrograms can be combined (e.g., linearly combined) to generate electrograms, again including activation timing information, in any direction of the plane of catheter 13 by computing an E-field loop for a clique of electrodes. U.S. application Ser. No. 15/953,155, which is hereby incorporated by reference as though fully set forth herein, discloses details of computing an E-field loop for a clique of electrodes on a HD grid catheter.

In any event, catheter 13 can be used to simultaneously collect a plurality of electrophysiology data points for the various bipoles defined by electrodes 17 thereon, with each such electrophysiology data point including both localization information (e.g., position and orientation of a selected bipole) and an electrogram signal for the selected bipole. For purposes of illustration, methods according to the instant disclosure will be described with reference to individual electrophysiology data points collected by catheter 13. It should be understood, however, that the teachings herein can be applied, in serial and/or in parallel, to multiple electrophysiology data points collected by catheter 13.

Catheter 13 (or multiple such catheters) are typically introduced into the heart and/or vasculature of the patient via one or more introducers and using familiar procedures. Indeed, various approaches to introduce catheter 13 into a patient's heart, such as transseptal approaches, will be familiar to those of ordinary skill in the art, and therefore need not be further described herein.

Since each electrode 17 lies within the patient, location data may be collected simultaneously for each electrode 17 by system 8. Similarly, each electrode 17 can be used to gather electrophysiological data from the cardiac surface (e.g., surface electrograms). The ordinarily skilled artisan will be familiar with various modalities for the acquisition and processing of electrophysiology data points (including, for example, both contact and non-contact electrophysiological mapping), such that further discussion thereof is not necessary to the understanding of the techniques disclosed herein. Likewise, various techniques familiar in the art can be used to generate a graphical representation of a cardiac geometry and/or of cardiac electrical activity from the plurality of electrophysiology data points. Moreover, insofar as the ordinarily skilled artisan will appreciate how to create electrophysiology maps from electrophysiology data points, the aspects thereof will only be described herein to the extent necessary to understand the present disclosure.

Returning now to FIG. 1, in some embodiments, an optional fixed reference electrode 31 (e.g., attached to a wall of the heart 10) is shown on a second catheter 29. For calibration purposes, this electrode 31 may be stationary (e.g., attached to or near the wall of the heart) or disposed in a fixed spatial relationship with the roving electrodes (e.g., electrodes 17), and thus may be referred to as a "navigational reference" or "local reference." The fixed reference electrode 31 may be used in addition or alternatively to the surface reference electrode 21 described above. In many instances, a coronary sinus electrode or other fixed electrode in the heart 10 can be used as a reference for measuring voltages and displacements; that is, as described below, fixed reference electrode 31 may define the origin of a coordinate system.

Each surface electrode is coupled to a multiplex switch 24, and the pairs of surface electrodes are selected by software running on a computer 20, which couples the surface electrodes to a signal generator 25. Alternately, switch 24 may be eliminated and multiple (e.g., three) instances of signal generator 25 may be provided, one for each measurement axis (that is, each surface electrode pairing).

The computer 20 may comprise, for example, a conventional general-purpose computer, a special-purpose computer, a distributed computer, or any other type of computer. The computer 20 may comprise one or more processors 28, such as a single central processing unit ("CPU"), or a plurality of processing units, commonly referred to as a parallel processing environment, which may execute instructions to practice the various aspects described herein.

Generally, three nominally orthogonal electric fields are generated by a series of driven and sensed electric dipoles (e.g., surface electrode pairs 12/14, 18/19, and 16/22) in order to realize catheter navigation in a biological conductor. Alternatively, these orthogonal fields can be decomposed and any pairs of surface electrodes can be driven as dipoles to provide effective electrode triangulation. Likewise, the electrodes 12, 14, 18, 19, 16, and 22 (or any number of electrodes) could be positioned in any other effective arrangement for driving a current to or sensing a current from an electrode in the heart. For example, multiple electrodes could be placed on the back, sides, and/or belly of patient 11. Additionally, such non-orthogonal methodologies add to the flexibility of the system. For any desired axis, the potentials measured across the roving electrodes resulting from a predetermined set of drive (source-sink) configurations may be combined algebraically to yield the same effective potential as would be obtained by simply driving a uniform current along the orthogonal axes.

Thus, any two of the surface electrodes 12, 14, 16, 18, 19, 22 may be selected as a dipole source and drain with respect to a ground reference, such as belly patch 21, while the unexcited electrodes measure voltage with respect to the ground reference. The roving electrodes 17 placed in the heart 10 are exposed to the field from a current pulse and are measured with respect to ground, such as belly patch 21. In practice the catheters within the heart 10 may contain more or fewer electrodes than the sixteen shown, and each electrode potential may be measured. As previously noted, at least one electrode may be fixed to the interior surface of the heart to form a fixed reference electrode 31, which is also measured with respect to ground, such as belly patch 21, and which may be defined as the origin of the coordinate system relative to which system 8 measures positions. Data sets from each of the surface electrodes, the internal electrodes, and the virtual electrodes may all be used to determine the location of the roving electrodes 17 within heart 10.

The measured voltages may be used by system 8 to determine the location in three-dimensional space of the electrodes inside the heart, such as roving electrodes 17 relative to a reference location, such as reference electrode 31. That is, the voltages measured at reference electrode 31 may be used to define the origin of a coordinate system, while the voltages measured at roving electrodes 17 may be used to express the location of roving electrodes 17 relative to the origin. In some embodiments, the coordinate system is a three-dimensional (x, y, z) Cartesian coordinate system, although other coordinate systems, such as polar, spherical, and cylindrical coordinate systems, are contemplated.

As should be clear from the foregoing discussion, the data used to determine the location of the electrode(s) within the heart is measured while the surface electrode pairs impress an electric field on the heart. The electrode data may also be used to create a respiration compensation value used to improve the raw location data for the electrode locations as described, for example, in U.S. Pat. No. 7,263,397, which is hereby incorporated herein by reference in its entirety. The electrode data may also be used to compensate for changes in the impedance of the body of the patient as described, for example, in U.S. Pat. No. 7,885,707, which is also incorporated herein by reference in its entirety.

Therefore, in one representative embodiment, system 8 first selects a set of surface electrodes and then drives them with current pulses. While the current pulses are being delivered, electrical activity, such as the voltages measured with at least one of the remaining surface electrodes and in vivo electrodes, is measured and stored. Compensation for artifacts, such as respiration and/or impedance shifting, may be performed as indicated above.

In aspects of the disclosure, system 8 can be a hybrid system that incorporates both impedance-based (e.g., as described above) and magnetic-based localization capabilities. Thus, for example, system 8 can also include a magnetic source 30, which is coupled to one or more magnetic field generators. In the interest of clarity, only two magnetic field generators 32 and 33 are depicted in FIG. 1, but it should be understood that additional magnetic field generators (e.g., a total of six magnetic field generators, defining three generally orthogonal axes analogous to those defined by patch electrodes 12, 14, 16, 18, 19, and 22) can be used without departing from the scope of the present teachings. Likewise, those of ordinary skill in the art will appreciate that, for purposes of localizing catheter 13 within the magnetic fields so generated, can include one or more magnetic localization sensors (e.g., coils).

In some embodiments, system 8 is the EnSite™ Velocity™ or EnSite Precision™ cardiac mapping and visualization system of Abbott Laboratories. Other localization systems, however, may be used in connection with the present teachings, including for example the RHYTHMIA HDX™ mapping system of Boston Scientific Corporation (Marlborough, Massachusetts), the CARTO navigation and location system of Biosense Webster, Inc. (Irvine, California), the AURORA® system of Northern Digital Inc. (Waterloo, Ontario), Sterotaxis, Inc.'s NIOBE® Magnetic Navigation System (St. Louis, Missouri), as well as MediGuide™ Technology from Abbott Laboratories.

The localization and mapping systems described in the following patents (all of which are hereby incorporated by reference in their entireties) can also be used with the present invention: U.S. Pat. Nos. 6,990,370; 6,978,168; 6,947,785; 6,939,309; 6,728,562; 6,640,119; 5,983,126; and 5,697,377.

Aspects of the disclosure relate to electrophysiological mapping, and in particular to generating visualizations (that is, graphical representations) of LAT maps. Such visualizations can be output, for example, on display 23. System 8 can therefore include a visualization module 58 that can be used to generate an LAT map and output the same (e.g., on display 23).

One exemplary method according to the present teachings will be explained with reference to the flowchart 400 of representative steps presented as FIG. 4. In some embodiments, for example, flowchart 400 may represent several exemplary steps that can be carried out by electroanatomical mapping system 8 of FIG. 1 (e.g., by processor 28 and/or visualization module 58). It should be understood that the representative steps described below can be either hardware- or software-implemented. For the sake of explanation, the term "signal processor" may be used herein to describe both hardware- and software-based implementations of the teachings herein.

In block 402, system 8 receives an LAT data set (which can also be referred to as an "LAT map"). As those of ordinary skill in the art will appreciate, the LAT data set includes a plurality of electrophysiology (EP) data points, each of which includes both localization information and an electrogram signal. For instance, in embodiments of the disclosure, the localization information corresponds to the median position of catheter 13 during collection of the corresponding electrogram signal.

The ordinarily skilled artisan will also appreciate that the LAT data set can be represented graphically (e.g., on display 23) on a model of a cardiac surface. For instance, United States patent application publication no. 2007/0073179, which is hereby incorporated by reference as though fully set forth herein, describes the projection of electrophysiology information (including, but not limited to, LAT information) from EP data points onto a cardiac surface model. Likewise, it is known to project only electrophysiology information from EP data points having localization information within a preset threshold distance of the cardiac surface model, and to discard all other EP data points, in order to reduce redundancy and map variability. Once the EP data points have been projected onto the cardiac surface model, they can be annotated with LAT information, for example in accordance with the teachings of United States patent application publication no. 2019/0038165, which is hereby incorporated by reference as though fully set forth herein.

Figure 5:
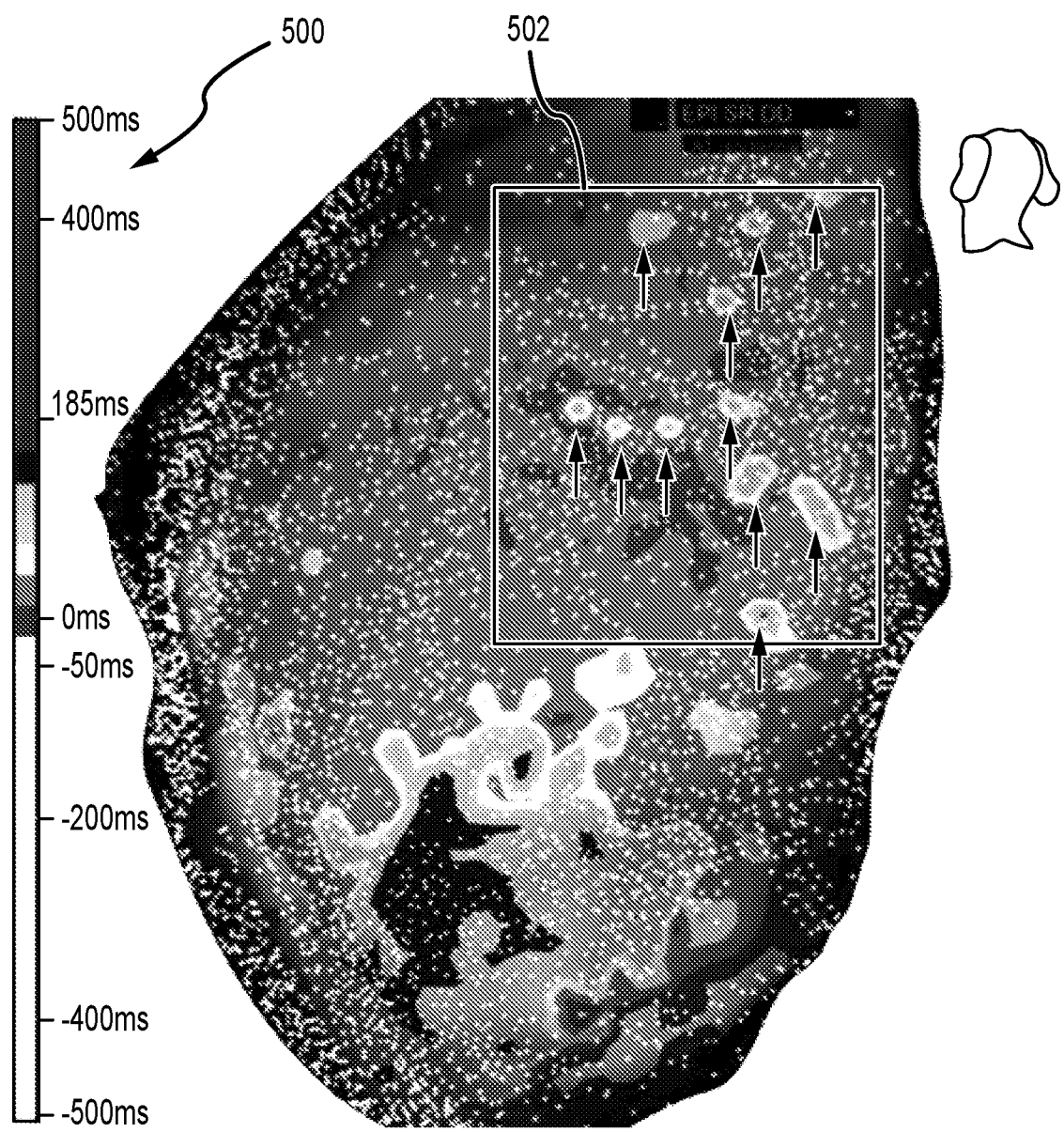
FIG. 5 is an exemplary graphical representation of local activation time data prior to application of the techniques and teachings disclosed herein.

FIG. 5 illustrates a graphical representation 500 of an LAT map, created using techniques that will be familiar to those of ordinary skill in the art. FIG. 5 also depicts a region 502 of outliers.

Figure 4:
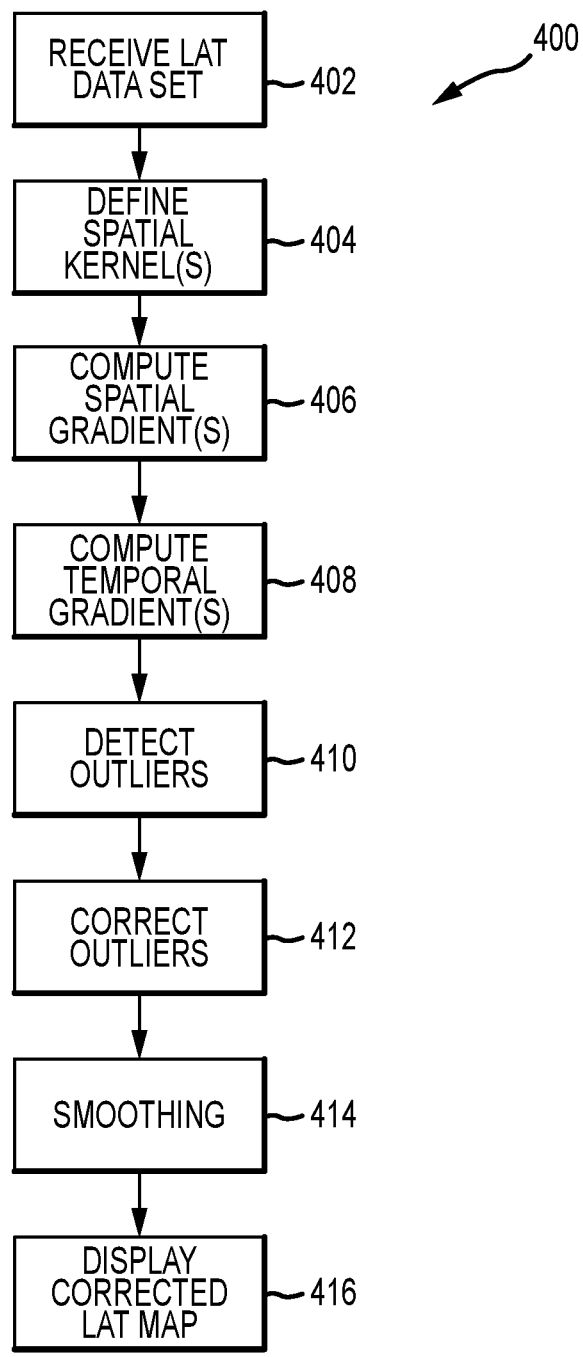
FIG. 4 is a flowchart of representative steps that can be carried out in generating a graphical representation of local activation times according to exemplary embodiments disclosed herein.

Returning now to flowchart 400 in FIG. 4, in block 404, system 8 defines one or more spatial kernels (SK). According to aspects of the disclosure, each spatial kernel (denoted i) is defined as a sphere of radius r centered on a given EP data point (denoted $DxL^{i,0}$). Each spatial kernel i is further defined to include the N additional EP data points (each denoted $DxL_{i,j}$, where j is between 1 and N) that are within radius r of $DxL^{i,0}$ (measured, for example, using the three-dimensional geodesic distance d between $DxL^{i,0}$ and $DxL^{i,j}$). The radius r can be user-preset; in certain embodiments of the disclosure, r is about 5 mm.

Figure 6A:
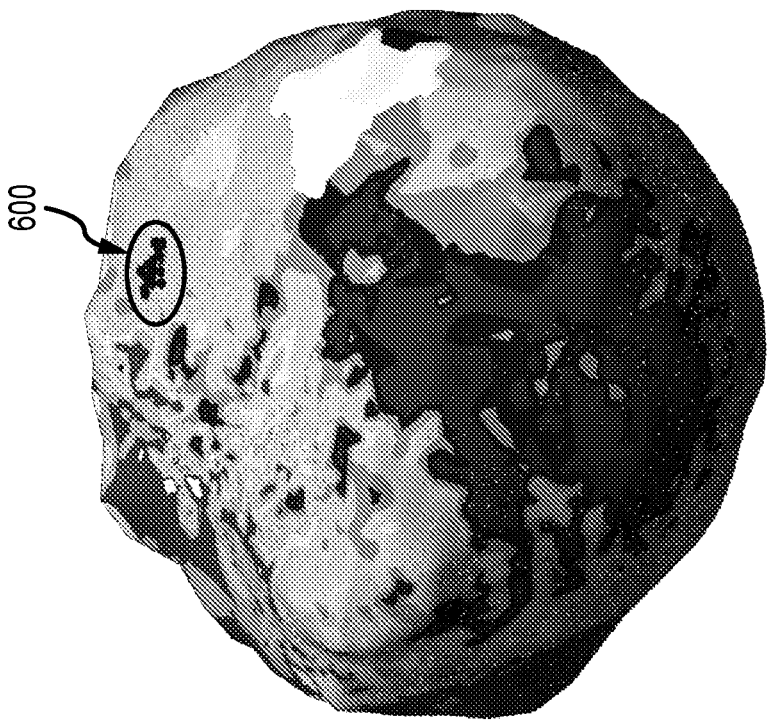
FIGS. 6A and 6B depict spatial kernels according to aspects of the instant disclosure.

In block 406, system 8 computes a spatial gradient for each defined spatial kernel. In certain embodiments of the disclosure, a spatial kernel can be defined, and thus a spatial kernel computed, for each EP data point. This is shown, for example, as spatial kernel 600 in FIG. 6A.

In other embodiments of the disclosure, spatial kernels are only defined, and spatial gradients only computed, for a subset of the EP data points. For instance, system 8 can accept user input selecting a subset of the EP data points for spatial kernel definition and spatial gradient computation.

Figure 6B:
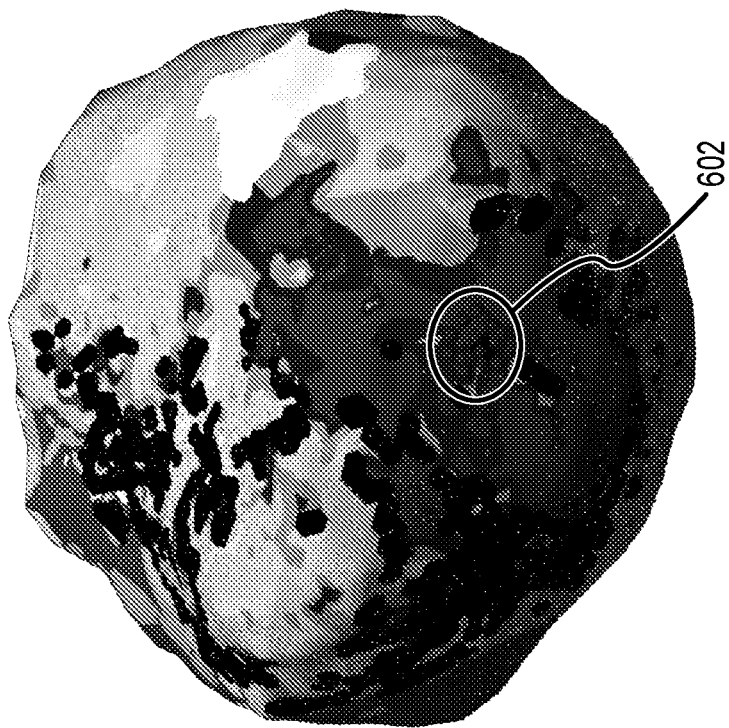

Alternatively, system 8 can determine the subset of EP data points for spatial kernel definition and spatial gradient computation analytically. For instance, system 8 can apply a filter, such as the vtkGradientFilter (https://vtk.org/doc/nightly/html/classytkGradientFilter.html), to identify one or more high-LAT gradient regions. Of course, computational efficiency can be improved by defining spatial kernels and computing spatial gradients only within these identified high-LAT gradient regions. This is shown, for example, as spatial kernel 602 in FIG. 6B, which also depicts high-LAT gradient regions as dark black patches on the cardiac surface model.

Regardless of the approach to defining spatial kernels (e.g., all EP data points, user-selected subset of EP data points, analytically-determined subset of EP data points, or any other suitable approach), the spatial gradient for spatial kernel i can be computed as $SK\_Grad^i = \{LAT \text{ at } DxL^{i,0}\}$ — median(A), where median(A) is the median of the set A={LAT at $DxL^{i,j}$=1 to N}. Note that the mean and/or standard deviation of set A can also be computed.

In block 408, system 8 computes a temporal gradient for each EP data point (denoted $DxL^{i,0}$). The temporal gradient is computed over several beats, such as about 20 seconds. Thus, a temporal kernel for $DxL^{i,0}$ can be defined to include NT additional beats (each denoted $DxL^{i,m}$, where m is between 1 and NT) that are morphologically similar (e.g., with respect to ECG and/or electrogram signals), to the electrogram signal for $DxL^{i,0}$. Those of ordinary skill in the art will be familiar with various approaches to computing the morphological similarity between signals (e.g., through the use of cross-correlation). It is also contemplated, however, to use the peak frequency functions of the signals, discussed in greater detail below, as a measure of morphological similarity.

A proximity criterion (e.g., the beat was measured at a location within about 5 mm of $DxL^{i,0}$) can also be used when defining the temporal kernel.

For each temporal kernel (and thus for each EP data point), a temporal gradient can be computed as $TK\_Grad^i = \{LAT \text{ at } DxL^{i,0}\}$ — median(B), where median(B) is the median of the set B={LAT at $DxL^{i,m}$, m=1 to NT}. Note that the mean and/or standard deviation of set B can also be computed.

System 8 detects outliers in block 410. More particularly, system 8 detects spatial outliers using the spatial gradients computed in block 406 and detects temporal outliers using the temporal gradients computed in block 408. In either case, system 8 can detect that the EP data point anchoring a spatial kernel (e.g., $DxL^{i,0}$) or temporal kernel (e.g., $DxL^{i,0}$) is an outlier by comparing the computed spatial gradient (e.g., $SK\_Grad^i$) or temporal gradient (e.g., $TK\_Grad^i$) to a corresponding spatial gradient threshold or temporal gradient threshold; if the computed spatial or temporal gradient exceeds the corresponding threshold, then the anchoring EP data point can be identified as an outlier.

In some aspects of the disclosure, the spatial gradient threshold and/or the temporal gradient threshold are user-preset values, such as about 50 ms. In other aspects of the disclosure, the spatial gradient threshold and/or the temporal gradient threshold are computed as a scaled median absolute deviation (MAD) of set A and set B, respectively. In particular embodiments of the disclosure, MAD(A)=c*median (|LAT at DxL$^{i,j}$−median(A)|) for j=1 to N and MAD(B)= c*median(|LAT at DxL$^{l,m}$−median(B)|) for m=1 to NT, where c=1.4826.

Figure 7:
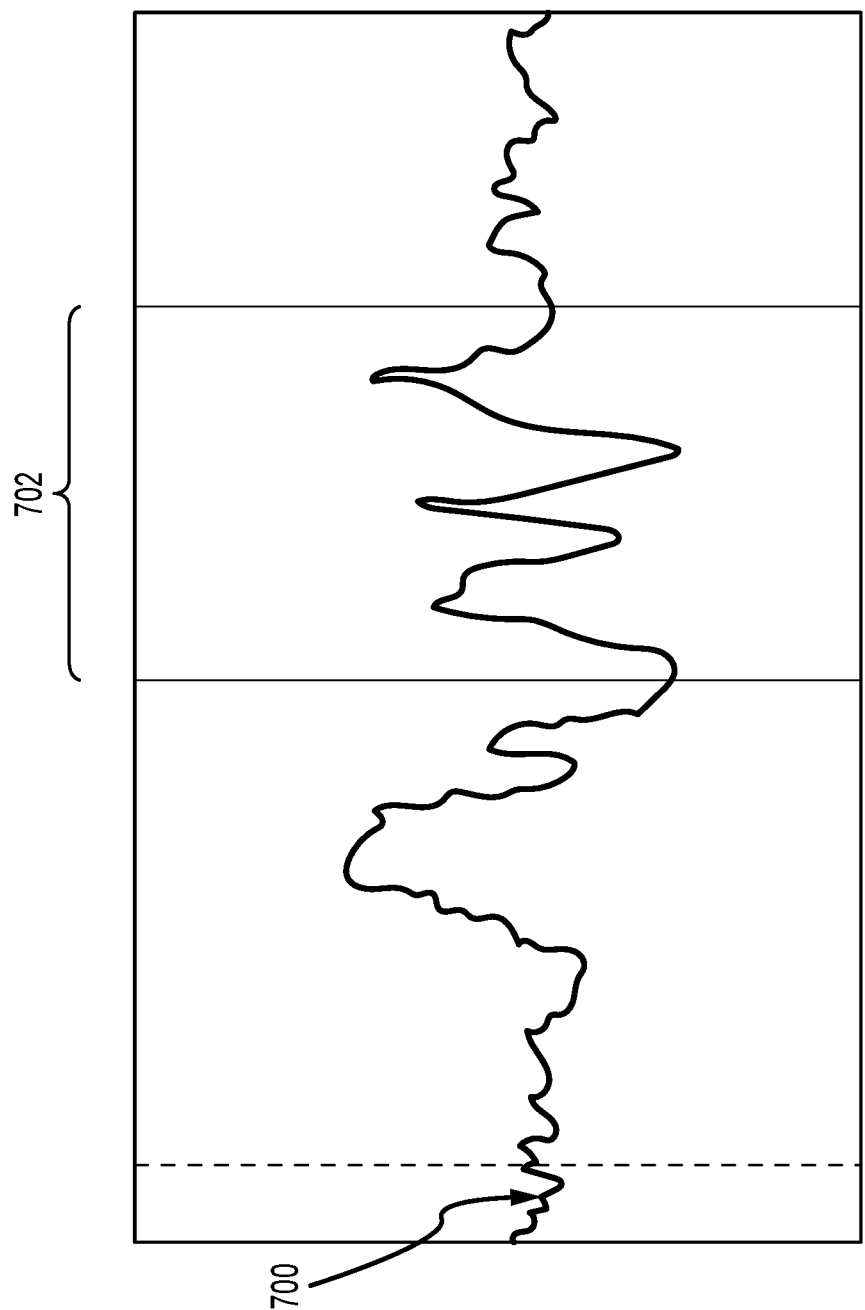
FIG. 7 illustrates a windowed electrogram for an outlier EP data point.

System 8 corrects outliers in block 412. In some embodiments, system 8 applies a LAT value dispersion algorithm to correct outliers. Electrogram signals for spatial outlier EP data points DxL$^{i,0}$ are windowed using mean(A)±std_dev (A), while electrogram signals for temporal outlier EP data points DxL$^{l,0}$ are windowed using mean(B)±std_dev(B). FIG. 7 illustrates an electrogram signal 700 for an outlier EP data point windowed 702 as described above.

Figure 8:
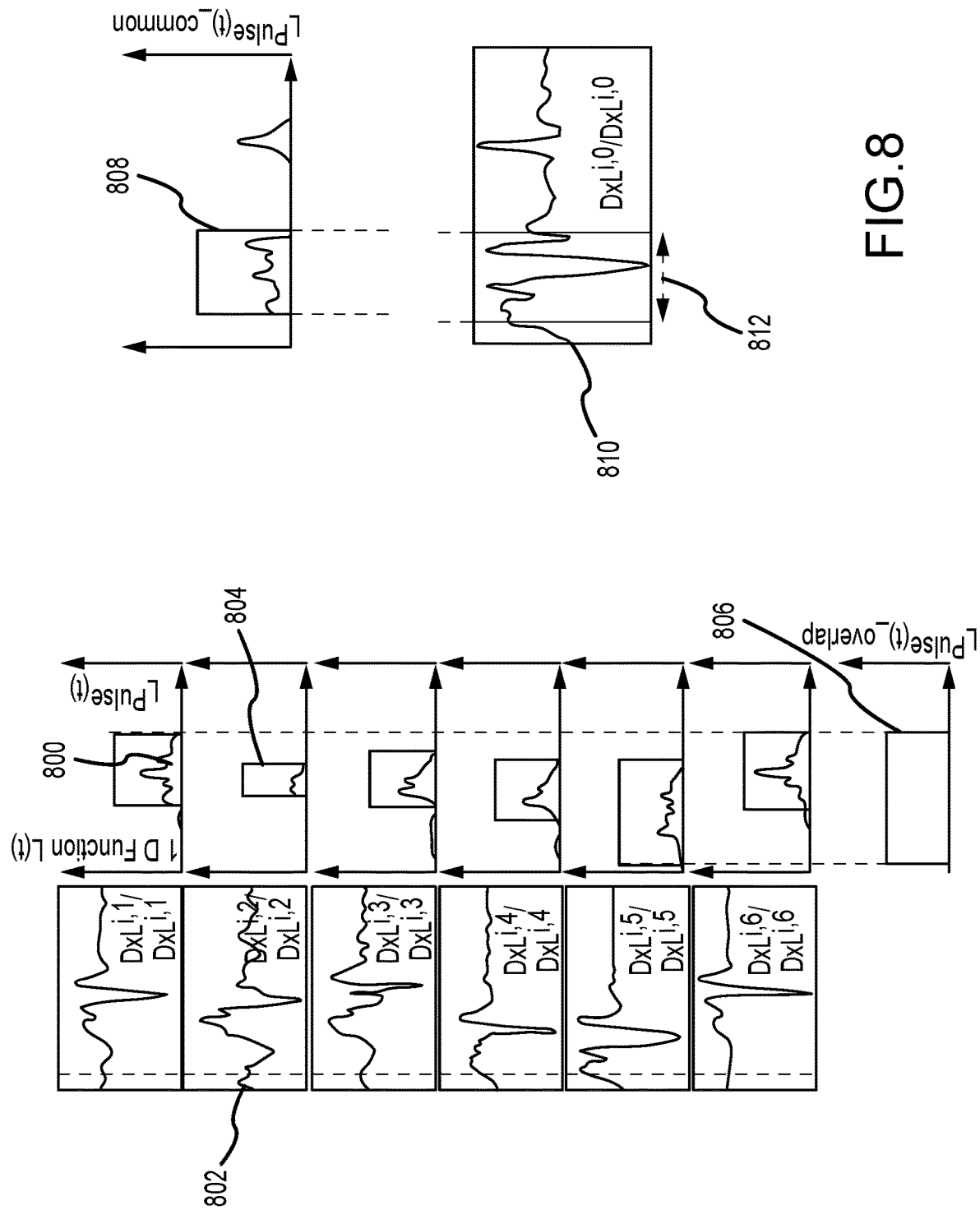
FIG. 8 illustrates application of a peak frequency dispersion algorithm to an electrogram for an outlier EP data point.

In other embodiments, system 8 applies a peak frequency dispersion algorithm to correct outliers. FIG. 8 illustrates the peak frequency dispersion algorithm. First, one-dimensional energy functions L(t) 800 of the electrograms 802 for the spatial and/or temporal kernels of outlier EP data points are computed, for example as disclosed in United States patent application publication no. 2019/0038165. Each energy function 800 is then converted to a step function 804

$$L^{Pulse}(t) = \begin{cases} 1, & \text{if } L(t) > 0 \\ 0, & \text{elsewhere} \end{cases}.$$

Once all step functions $L^{Pulse}(t)$ are computed for a particular kernel, an overlap function 806 $L^{Pulse}(t)$_overlap is computed.

Next, the step functions $L^{Pulse}(t)$ and overlap function $L^{Pulse}(t)$_overlap are combined using Boolean operations to identify the common subset of the functions $L^{Pluse}(t)$_common (e.g., 808). $L^{Pulse}(t)$_common 808 is applied to the electrogram signal 810 for the outlier EP data point as the window of interest 812.

Under either approach, a corrected LAT for the outlier EP data point can be computed on the windowed electrogram signal, for example using the teachings of United States patent application publication no. 2019/0038165.

Where neither LAT value dispersion nor peak frequency dispersion yields a valid corrected LAT, median(A) can be used as the corrected LAT for a spatial outlier EP data point, while median(B) can be used as the corrected LAT for a temporal outlier EP data point.

Spatial outlier EP data point LATs can also be smoothed in block 414. According to embodiments disclosed herein, the LATs at spatial outlier EP data points are smoothed by applying a Gaussian distribution to the corresponding spatial kernel. For instance, the smoothened LAT at a spatial outlier EP data point DxL$^{i,0}$ can be computed as $$\frac{\sum (W^j * A)}{\sum W^j},$$

where $$W^j = \frac{1}{\sqrt{(2\pi\sigma)}} * \exp\left(-\frac{(LAT \text{ at } DxL^{i,j} - \mu)^2}{\sigma^2}\right),$$

exp is exponential, and μ and σ are user-preset parameters to control the shape of the Gaussian distribution. In embodiments of the disclosure, μ and σ are about 1.0 and about 2.0, respectively.

Figure 9B:
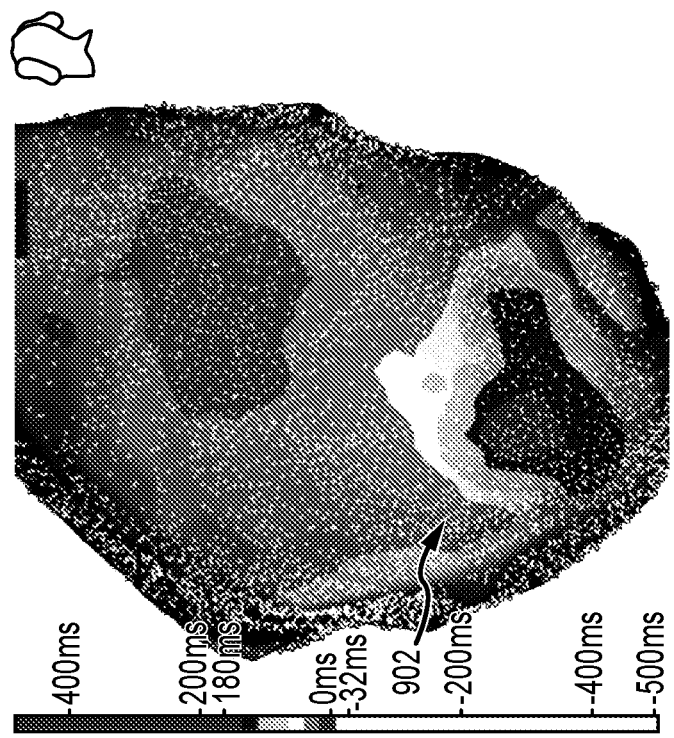
FIGS. 9A and 9B illustrate corrected LAT maps, as may be generated through application of the teachings herein.
Figure 9A:
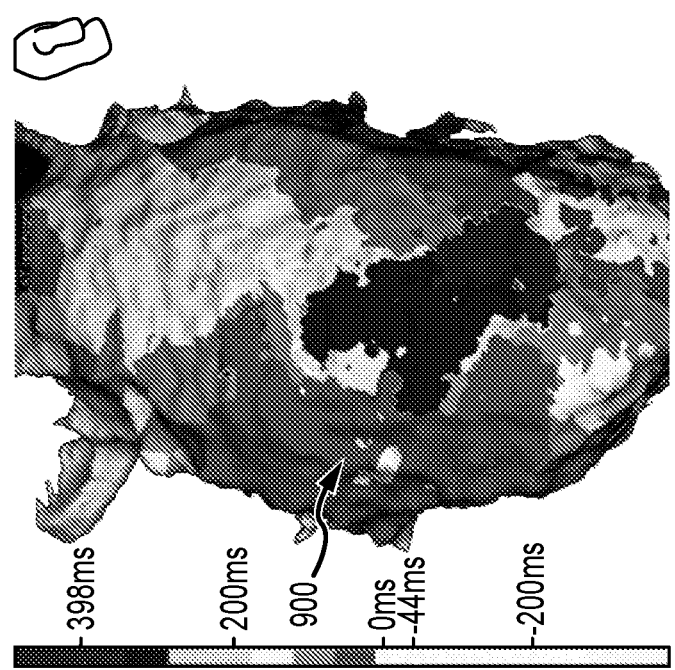

As illustrated in FIGS. 9A and 9B, system 8 outputs a graphical representation of the corrected LAT map, in block 416. In particular, FIG. 9A illustrates a graphical representation 900 of a corrected LAT map, while FIG. 9B illustrates a graphical representation 902 of a corrected and smoothed LAT map.

Although several embodiments have been described above with a certain degree of particularity, those skilled in the art could make numerous alterations to the disclosed embodiments without departing from the spirit or scope of this invention.

For example, the teachings herein can be applied in real time (e.g., during an electrophysiology study) or during post-processing (e.g., to electrophysiology data points collected during an electrophysiology study performed at an earlier time).

All directional references (e.g., upper, lower, upward, downward, left, right, leftward, rightward, top, bottom, above, below, vertical, horizontal, clockwise, and counter-clockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of graphically representing local activation time (LAT), the method comprising:
    receiving from a multi-electrode electrophysiology catheter, at an electroanatomical mapping system, the electroanatomical mapping system including a display, an LAT data set comprising a plurality of electrophysiology (EP) data points, wherein each EP data point of the plurality of EP data points includes localization information and an electrogram signal;
    the electroanatomical mapping system computing a spatial gradient over a spatial kernel centered at an EP data point of the plurality of EP data points of the LAT data set;
    the electroanatomical mapping system computing a respective temporal gradient for each of the plurality of EP data points of the LAT data set, thereby computing a plurality of temporal gradients;
    the electroanatomical mapping system detecting a spatial outlier EP data point within the spatial kernel using the spatial gradient;
    the electroanatomical mapping system detecting a temporal outlier EP data point using the plurality of temporal gradients;
    the electroanatomical mapping system correcting the spatial outlier EP data point and the temporal outlier EP data point, thereby creating a corrected LAT map; and
    the electroanatomical mapping system outputting to the display a graphical representation of the corrected LAT map on a model of a cardiac surface.

2. The method according to claim 1, wherein receiving from a multi-electrode electrophysiology catheter, at an electroanatomical mapping system, an LAT data set comprising a plurality of electrophysiology (EP) data points, comprises:
projecting each EP data point onto the model of the cardiac surface using the localization information for the respective EP data point; and
assigning a LAT to each projected EP data point using the electrogram signal for the respective EP data point.

3. The method according to claim 1, wherein the electroanatomical mapping system computing a spatial gradient over a spatial kernel centered at an EP data point of the plurality of EP data points of the LAT data set comprises:
defining a spatial kernel for each EP data point of the plurality of EP data points; and
computing a spatial gradient for each defined spatial kernel.

4. The method according to claim 1, wherein the electroanatomical mapping system computing a spatial gradient over a spatial kernel centered at an EP data point of the plurality of EP data points of the LAT data set comprises:
the electroanatomical mapping system accepting user input selecting a subset of the plurality of EP data points;
defining a spatial kernel for each EP data point of the subset of the plurality of EP data points; and
computing a spatial gradient for each defined spatial kernel.

5. The method according to claim 1, wherein the electroanatomical mapping system computing a spatial gradient over a spatial kernel centered at an EP data point of the plurality of EP data points of the LAT data set comprises:
the electroanatomical mapping system identifying a high LAT gradient region within the LAT data set;
defining a spatial kernel for each EP data point within the high LAT gradient region; and
computing a spatial gradient for each defined spatial kernel.

6. The method according to claim 1, wherein the electroanatomical mapping system detecting a spatial outlier EP data point within the spatial kernel using the spatial gradient comprises the electroanatomical mapping system detecting the spatial outlier EP data point by comparing the spatial gradient to a spatial gradient threshold.

7. The method according to claim 6, wherein the spatial gradient threshold comprises a user-preset value.

8. The method according to claim 6, wherein the spatial gradient threshold comprises a computed scaled mean absolute deviation value.

9. The method according to claim 1, wherein the electroanatomical mapping system detecting a temporal outlier EP data point using the plurality of temporal gradients comprises the electroanatomical mapping system detecting the temporal outlier EP data point by comparing the plurality of temporal gradients to a temporal gradient threshold.

10. The method according to claim 9, wherein the temporal gradient threshold comprises a user-preset value.

11. The method according to claim 9, wherein the temporal gradient threshold comprises a computed scaled mean absolute deviation value.

12. The method according to claim 1, wherein the electroanatomical mapping system correcting the spatial outlier EP data point and the temporal outlier EP data point, thereby creating a corrected LAT map, comprises the electroanatomical mapping system applying at least one of a LAT value dispersion algorithm and a peak frequency dispersion algorithm to the spatial outlier EP data point and the temporal outlier EP data point.

13. The method according to claim 1, further comprising the electroanatomical mapping system spatially smoothing the LAT data set.

14. The method according to claim 13, wherein the electroanatomical mapping system spatially smoothing the LAT data set comprises applying a Gaussian distribution to the spatial kernel.

15. A method of graphically representing local activation time (LAT), comprising:
receiving, at an electroanatomical mapping system, the electroanatomical mapping system including a multi-electrode electrophysiology catheter and a display, an LAT map, the LAT map including a plurality of electrophysiology (EP) data points;
the electroanatomical mapping system identifying at least one of a spatial outlier EP data point and a temporal outlier data point within the plurality of EP data point by:
computing a spatial gradient over a spatial kernel centered at an EP data point of the plurality of EP data points;
computing a temporal gradient over a temporal kernel for the EP data point of the plurality of EP data points; and
identifying the at least one of the spatial outlier EP data point and the temporal outlier EP data point using the computed spatial gradient and the computed temporal gradient;
the electroanatomical mapping system correcting the identified at least one of the spatial outlier EP data point and the temporal outlier EP data point, thereby creating a corrected LAT map; and
the electroanatomical mapping system outputting to the display a graphical representation of the corrected LAT map on a model of a cardiac surface.

16. The method according to claim 15, wherein the electroanatomical mapping system correcting the identified at least one of the spatial outlier EP data point and the temporal outlier EP data point, thereby creating a corrected LAT map, comprises the electroanatomical mapping system applying at least one of a LAT value dispersion algorithm and a peak frequency dispersion algorithm to the at least one of the spatial outlier EP data point and the temporal outlier EP data point.

17. A system for graphically representing local activation time (LAT), comprising:
a display;
a visualization module configured to:
receive an LAT data set comprising a plurality of electrophysiology (EP) data points, wherein each EP data point of the plurality of EP data points includes localization information and an electrogram signal;
compute a spatial gradient over a spatial kernel centered at an EP data point of the plurality of EP data points of the LAT data set;
compute a respective temporal gradient for each of the plurality of EP data points of the LAT data set, thereby computing a plurality of temporal gradients;
detect a spatial outlier EP data point within the spatial kernel using the spatial gradient;
detect a temporal outlier EP data point using the plurality of temporal gradients;
correct the spatial outlier EP data point and the temporal outlier EP data point, thereby creating a corrected LAT map; and
output to the display a graphical representation of the corrected LAT map on a model of a cardiac surface.

18. The system according to claim 17, wherein the visualization module is configured to:
  identify a high LAT gradient region within the LAT data set; and
  compute a plurality of spatial gradients over a respective plurality of spatial kernels, each of the plurality of spatial kernels centered at a respective EP data point within the high LAT gradient region.

19. The system according to claim 17, wherein the visualization module is configured to correct the spatial outlier EP data point and the temporal outlier EP data point by applying at least one of a LAT value dispersion algorithm and a peak frequency dispersion algorithm to the spatial outlier EP data point and the temporal outlier EP data point.

\* \* \* \* \*